United States Patent
Wang et al.

(10) Patent No.: US 10,484,629 B2
(45) Date of Patent: Nov. 19, 2019

(54) SINGLE IMAGE SENSOR FOR CAPTURING MIXED STRUCTURED-LIGHT IMAGES AND REGULAR IMAGES

(71) Applicant: CapsoVision, Inc, Saratoga, CA (US)

(72) Inventors: Kang-Huai Wang, Saratoga, CA (US); Yi Xu, Menlo Park, CA (US); Gordon C. Wilson, San Francisco, CA (US); Chenyu Wu, Sunnyvale, CA (US)

(73) Assignee: CAPSO VISION INC, Saratoga, CA (US)

( * ) Notice: Subject to any disclaimer, the term of this patent is extended or adjusted under 35 U.S.C. 154(b) by 289 days.

(21) Appl. No.: 15/333,071

(22) Filed: Oct. 24, 2016

(65) Prior Publication Data

US 2017/0109890 A1 Apr. 20, 2017

Related U.S. Application Data

(63) Continuation-in-part of application No. 14/884,788, filed on Oct. 16, 2015, now Pat. No. 9,936,151.
(Continued)

(51) Int. Cl.
*H04N 5/355* (2011.01)
*H04N 5/225* (2006.01)
(Continued)

(52) U.S. Cl.
CPC ..... *H04N 5/35581* (2013.01); *G01B 11/2513* (2013.01); *G06T 7/521* (2017.01);
(Continued)

(58) Field of Classification Search
CPC ............. H04N 5/2256; H04N 5/35581; H04N 5/2255; H04N 13/254; H04N 13/271; H04N 13/296; H04N 2005/2255
(Continued)

(56) References Cited

U.S. PATENT DOCUMENTS 7,983,458 B2 7/2011 Wang et al.
2005/0219552 A1* 10/2005 Ackerman ............. A61B 1/042
356/603

(Continued)

OTHER PUBLICATIONS

"Structured-light 3D surface imaging: a tutorial", Geng, in Advances in Optics and Photonics, vol. 3, Issue 2, pp. 128-160, Mar. 31, 2011.
(Continued)

*Primary Examiner* — Tat C Chio
*Assistant Examiner* — Kathleen V Nguyen
(74) *Attorney, Agent, or Firm* — Blairtech Solution LLC

(57) ABSTRACT

A method and device for improving the accuracy of depth information derived from a structured-light image for a regular image are disclosed. In one example, an additional structured-light image is captured before a first structured-light image or after a regular image. The depth information for the regular image can be derived from the first structured-light image and corrected by incorporating depth information from the additional structured-light image. A model for depth information can be used to predict or interpolate depth information for the regular image. In another example, two regular sub-images may be captured with a structured-light image in between. If substantial frame differences or substantial global motion vector/block motion vectors are detected, the two regular sub-images will not be combined in order to avoid possible motion smear. Instead, one of the two sub-images will be selected and scaled as the output regular image.

7 Claims, 7 Drawing Sheets

Related U.S. Application Data

(60) Provisional application No. 62/268,975, filed on Dec. 17, 2015.

(51) Int. Cl.

| | | |
|---|---|---|
| *H04N 13/271* | (2018.01) | |
| *G06T 7/521* | (2017.01) | |
| *G01B 11/25* | (2006.01) | |
| *H04N 5/353* | (2011.01) | |
| *H04N 9/04* | (2006.01) | |
| *G06T 7/55* | (2017.01) | |

(52) U.S. Cl.
CPC .............. *G06T 7/55* (2017.01); *H04N 5/2256* (2013.01); *H04N 5/3532* (2013.01); *H04N 9/045* (2013.01); *H04N 13/271* (2018.05); *H04N 2005/2255* (2013.01)

(58) Field of Classification Search
USPC .......................................................... 348/46
See application file for complete search history.

(56) References Cited

U.S. PATENT DOCUMENTS

| | | | |
|---|---|---|---|
| 2007/0225600 A1* | 9/2007 | Weibrecht | A61B 6/025 600/429 |
| 2012/0293627 A1* | 11/2012 | Ishii | G06T 3/4007 348/46 |
| 2013/0176426 A1* | 7/2013 | Ovsiannikov | H04N 5/3535 348/135 |

OTHER PUBLICATIONS

"3-D Computer Vision Using Structured Light: Design, Calibration and Implementation Issues" (DePiero et al., Advances in Computers, vol. 43, Jan. 1, 1996, pp. 243-278).

\* cited by examiner

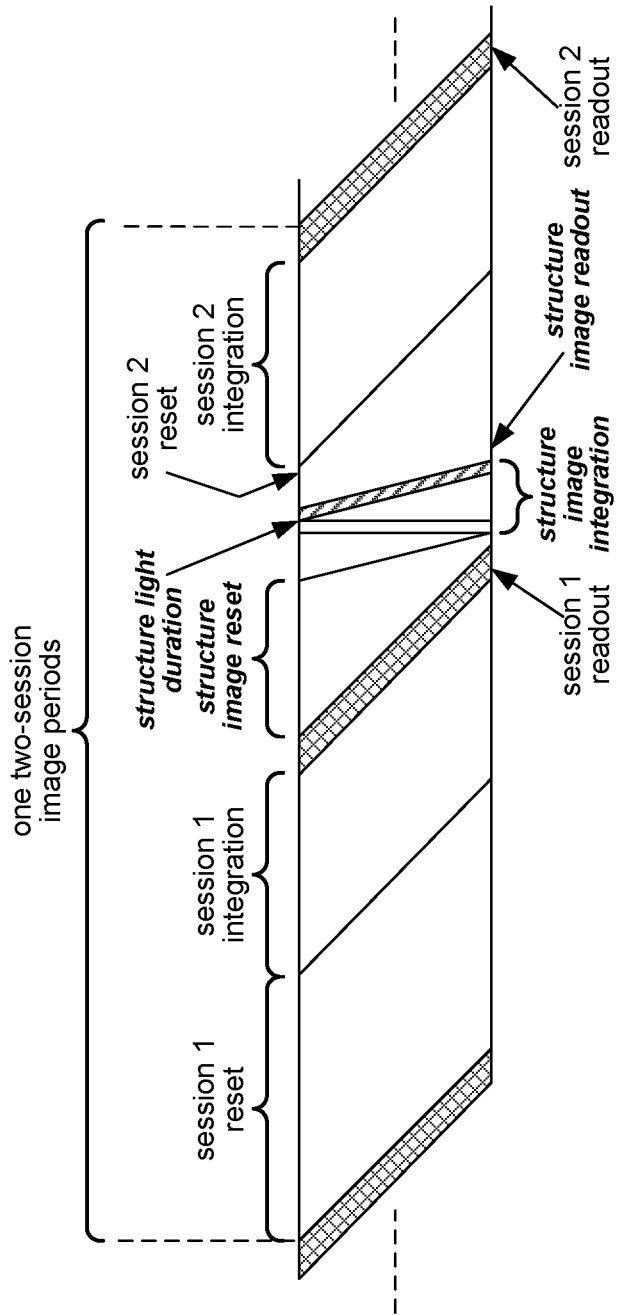

SINGLE IMAGE SENSOR FOR CAPTURING MIXED STRUCTURED-LIGHT IMAGES AND REGULAR IMAGES

CROSS REFERENCE TO RELATED APPLICATIONS

The present invention is a Nonprovisional application of and claims priority to U.S. Provisional Application Ser. No. 62/268,975, filed on Dec. 17, 2015. The present application is a Continuation-in-Part of and claims priority to U.S. patent application Ser. No. 14/884,788, filed on Oct. 16, 2015. The U.S. Provisional application and U.S. patent application are hereby incorporated by reference in their entireties.

FIELD OF THE INVENTION

The present invention relates to a single image sensor capable of capturing structured-light images and regular image, where the structured-light image is used to derive depth or shape information related to the corresponding regular image.

BACKGROUND AND RELATED ART

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Endoscopes allow a physician control over the field of view and are well-accepted diagnostic tools.

Capsule endoscope is an alternative in vivo endoscope developed in recent years. For capsule endoscope, a camera is housed in a swallowable capsule, along with a radio transmitter for transmitting data, primarily comprising images recorded by the digital camera, to a base-station receiver or transceiver and data recorder outside the body. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule.

An autonomous capsule camera system with on-board data storage was disclosed in the U.S. Pat. No. 7,983,458, entitled "In Vivo Autonomous Camera with On-Board Data Storage or Digital Wireless Transmission in Regulatory Approved Band," granted on Jul. 19, 2011. The capsule camera with on-board storage archives the captured images in on-board non-volatile memory. The capsule camera is retrieved upon its exiting from the human body. The images stored in the non-volatile memory of the retrieved capsule camera are then accessed through an output port on in the capsule camera.

While the two-dimensional images captured by the endoscopes have been shown useful for diagnosis, it is desirable to be able to capture gastrointestinal (GI) tract images with depth information (i.e., three-dimensional (3D) images) to improve the accuracy of diagnosis or to ease the diagnosis process. In the field of 3D imaging, 3D images may be captured using a regular camera for the texture information in the scene and a separate depth camera (e.g. Time of Flight camera) for the depth information of the scene in the field of view. The 3D images may also be captured using multiple cameras, where multiple cameras are often used in a planar configuration to capture a scene from different view angles. Then, point correspondence is established among multiple views for 3D triangulation. Nevertheless, these multi-camera systems may not be easily adapted to the GI tract environment, where the space is very limited. In the past twenty years, a structured light technology has been developed to derive the depth or shape of objects in the scene using a single camera. In the structured light system, a light source, often a projector is used to project known geometric pattern(s) onto objects in the scene. A regular camera can be used to capture images with and without the projected patterns. The images captured with the structured light can be used to derive the shapes associated with the objects in the scene. The depth or shape information is then used with regular images, which are captured with non-structured floodlit light, to create 3D textured model of the objects. The structured light technology has been well known in the field. For example, in "*Structured-light 3D surface imaging: a tutorial*" (Geng, in *Advances in Optics and Photonics*, Vol. 3, Issue 2, pp. 128-160, Mar. 31, 2011), structured light technology using various structured light patterns are described and the corresponding performances are compared. In another example, various design, calibration and implement issues are described in "3-D Computer Vision Using Structured Light: Design, Calibration and Implementation Issues" (DePiero et al., *Advances in Computers*, Volume 43, Jan. 1, 1996, pages 243-278). Accordingly, the details of the structured light technology are not repeated here.

While the structured light technology may be more suitable for 3D imaging of the GI tract than other technologies, there are still issues with the intended application for GI tract. For example, most of the structured light applications are intended for stationary object. Therefore, there is no object movement between the captured structured-light image and the regular image. Nevertheless, in the capsule camera application for GI tract imaging, both the capsule camera and the GI parts (e.g. small intestines and colons) may be moving. Therefore, there will be relative movement between the structured-light image and the regular image if they are captured consecutively. Furthermore, the capsule camera application is a very power-sensitive environment. The use of structured light will consume system power in addition to capturing the regular images. Besides, if one image with structured light is taken after each regular image, the useful frame rate will be dropped to half. If the same frame rate of regular images is maintained, the system would have to capture images at twice the regular frame rate and consume twice the power in image capture. Accordingly, it is desirable to develop technology for structured light application in the GI tract that can overcome these issues mentioned here.

BRIEF SUMMARY OF THE INVENTION

A method and device for improving the accuracy of depth information derived from structured-light image for a regular image are disclosed. In one embodiment, an additional structured-light image is captured before a first structured-light image or after a regular image. The depth information for the regular image can be derived from the first structured-light image and corrected by incorporating depth information from the additional structured-light image. A model for depth information can be used to predict or interpolate depth information for the regular image.

In another embodiment, two regular sub-images may be captured with a structured-light image in between. If substantial frame differences or substantial global motion vector/block motion vectors are detected, the two regular sub-images will not be combined to avoid possible motion smear. Instead, one of the two sub-images will be selected and scaled as output regular image. For example, the selected sub-image can be up-scaled by a factor of 2 and used as the output regular image. Other normalization techniques such as histogram equalization operation can also be applied.

In yet another embodiment, the pixel values of two regular sub-images, with a structured-light image in between, are processed by a non-linear transformation before the pixel values are combined to form a combined regular image. In one example, a compression point is selected. If the pixel value of the sub-images is greater than the compression point, the portion of pixel value exceeding the compression point is compressed by a factor (e.g. 2). The non-linear transformed pixel values for the sub-images are combined to form a combined regular image. Other non-linear transformation may also be used. For example, a piece-wise linear curve may be used to modify the pixel values of the regular sub-images.

This method of detecting the difference between two regular sub-images and deciding whether to combine them or not can also be applied to any regular image capture without the intervening structured-light image. Therefore, a regular camera system can take advantage of dynamic range expansion by applying non-linear transformation to pixel values of sub-images and combining the sub-images. Furthermore, whether to combine the two regular sub-images into one combined regular image or to output one selected sub-image without combination can be determined based on the differences between the two sub-images or global motion vector/block motion vectors detected between the two sub-images.

BRIEF DESCRIPTION OF THE DRAWINGS

FIG. 1A illustrates exemplary timing charts for capturing a two-session image according to an embodiment of the present invention, where a first regular sub-image is captured in the first session and a mixed image consisting of a structured-light image and a second regular sub-image is captured in the second session, the regular image are combined as the final output and the integration period for the first session is approximately the same as the integration period for the second session.

DETAILED DESCRIPTION OF THE INVENTION

Figure 1B:
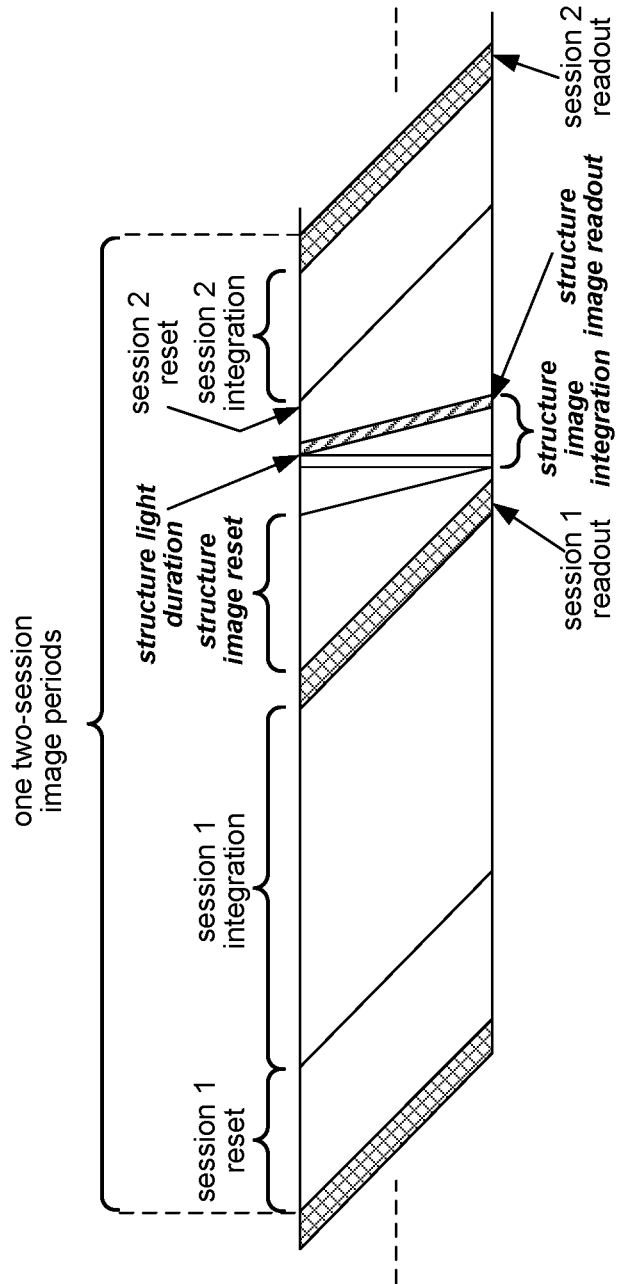
FIG. 1B illustrates exemplary timing charts similar to these of FIG. 7A, where the integration period for the first session is approximately three times as long as the integration period for the second session.

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely representative of selected embodiments of the invention. References throughout this specification to "one embodiment," "an embodiment," or similar language mean that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, or operations are not shown or described in detail to avoid obscuring aspects of the invention. The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

Endoscopes are normally inserted into the human body through a natural opening such as the mouth or anus. Therefore, endoscopes are preferred to be small sizes so as to be minimally invasive. To derive or capture the depth or shape information while capturing live images or videos of the GI tract with endoscopes, it is crucial to maintain the small-size form factor. Besides, with the small size and the capability to capture depth information along with corresponding images or video, such camera also finds its applications in other applications requiring compact size, such as a wearable devices.

One technique that may capture depth information is to use a color filter placed on top of selected sensor pixels with the passband reasonably narrow and capture the color information and depth information simultaneously. The environment light sources with spectrum in the filter passband will cause negligible amount of energy projected onto the sensor. For the case of RGB pixels, a fourth type of pixels may be added to capture light with the spectrum in the passband of the filter placed on top of these pixels. Then, the structured light that has the spectrum substantially in the passband can be projected onto the scene. However this approach will reduce the spatial resolution of the images or video captured using such image sensor.

Another technique is to obtain the depth information as well as 3D topology by projecting structured light patterns that are visible in the RGB sensors. However the real time image and/or video will be confounded by the structured light superimposed on it. This invention describes methods to use a single camera to achieve depth information by using the structured light approach while taking images or real time video using the camera.

As mentioned before, a conventional structured light approach with a single camera would incur several drawbacks. For example, the camera with a frame rate of 30 frames per second may be used. A conventional approach would take live video with interleaved images corresponding to images with and without the structured light. One issue is that the depth information is 1/30 second away from corresponding images to be viewed. If there is any movement in the scene, the depth information may not accurately represent the 3D topology of the corresponding images at 1/30 second away. In addition, the effective frame rate for the video to be viewed is dropped to 15 frames per second in this example.

In some video applications, the frame rate is crucial for the intended application. For example, a high frame-rate camera with frame rate in the 100's per second or more is required to capture video of fast moving objects such as a travelling bullet. In this case, the use of structured light would cut the frame rate to half and may hinder the intended application. For a capsule camera, the video for the gastro-intestinal (GI) tract is normally a few frames per second and the camera could be operating at twice the original frame rate to compensate the reduction of effective frame rate due to capturing structured-light images. However, it would result in twice as much power consumption, which is not desirable in the power-limited capsule environment.

A single sensor capable of capturing regular texture video as well as depth information associated with the corresponding texture video has been disclosed in U.S. patent application Ser. No. 14/884,788, filed on Oct. 16, 2015. According to U.S. patent application Ser. No. 14/884,788, the sensor system is arranged to capture a structured-light image and a regular image with shorter capture time for the structured-light image than that for the regular image. With the shorter capture time for the structured-light image, the time difference between the structured-light image and the corresponding regular image is shorter. Due to the shorter time difference between the structured-light image and the corresponding regular image, the depth information for the regular image derived from the corresponding structured-light image is more accurate.

The U.S. patent application Ser. No. 14/884,788, also discloses another arrangement to capture two regular sub-images with a structured-light image in between as shown in FIG. 1A and FIG. 1B. The two regular sub-images are combined into a single regular image. In FIG. 1A, the integration time for the two sub-images is roughly the same. However, the two integration time may also be different. For example, the integration time for the first sub-image may be three times as long as the integration time (also called integration period in this disclosure) for the second sub-image as shown in FIG. 1B. In this case, when the digital outputs from the two sub-images are combined, the combined image has the effect of weighted sum of the first sub-image (i.e., 3/4) and the second sub-image (1/4). There is no need to perform the weighted sum associated with different integration periods since the weighting will be reflected in the charges accumulated during respective integration periods. The longer integration period results in more accumulated charges, which result in a higher analog signal. Accordingly, the sum of the two digital readouts represents the weighted sum of the two sub-images, where the weighting factors correspond to the integration periods. Since the structured-light image is between the two regular sub-images, presumably the structured-light image is capable to capture even more accurate depth information for the corresponding regular image. Such sensor arrangement also provides the improved sensor dynamic range.

In the present invention, techniques to improve the performance of single sensor for capturing mixed structured-light images and regular images are disclosed. In U.S. patent application Ser. No. 14/884,788, the two regular sub-images with a structured-light image in between are combined to form a combined regular image. The underlying assumption is that the scene in the field of view (FOV) has little motion and the two regular sub-images are highly correlated. However, if the scene in the FOV contains substantial motion, the image contents of the two regular sub-images maybe very different in certain areas. Therefore, combining the two regular sub-images straightforward will result in motion smear in the combined regular image. Accordingly, in one embodiment of the present invention, if fast scene content change or some fast moving object in the scene is detected; either regular sub-image 1 or 2 is selected as output with some digital gain applied without combining the two. For example, if the integration time of regular sub-image 1 and regular sub-image 2 are the same, the digital gain can be set to 2.

The disparity in the two regular sub-images can be detected by using any existing disparity evaluation techniques such as frame differences measured in terms of mean squared error (MSE) or sum of absolution difference (SAD). Furthermore, quantitative motion information may also be measured and used to assist motion-compensated sub-image combination. For example, global motion vector between the two regular sub-images or block-based motion vectors between the two regular sub-images on a block basis can be measured and used for motion-compensated sub-image combination.

Alternatively, some processing technique may be applied to the selected regular sub-image to scale the sub-image. For example, histogram equalization can be applied to the selected regular sub-image.

Figure 2:
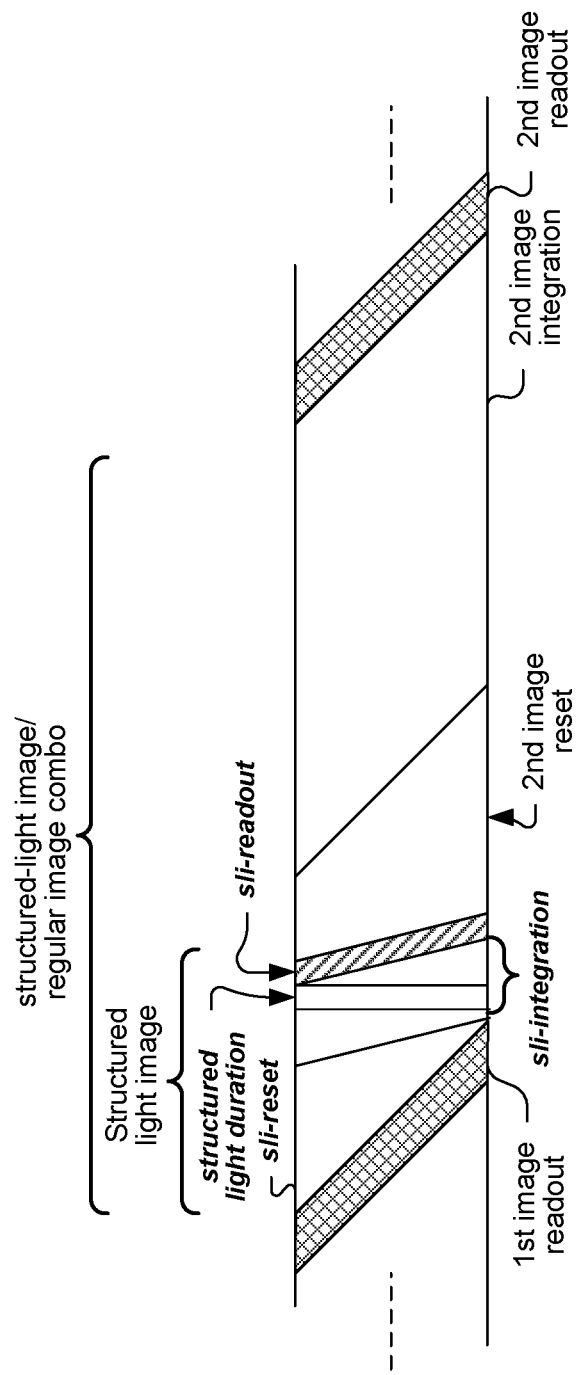
FIG. 2 illustrates another view of applying the structured light for capturing a structured-light image and capturing a regular image according to an embodiment of the present invention.
Figure 3:
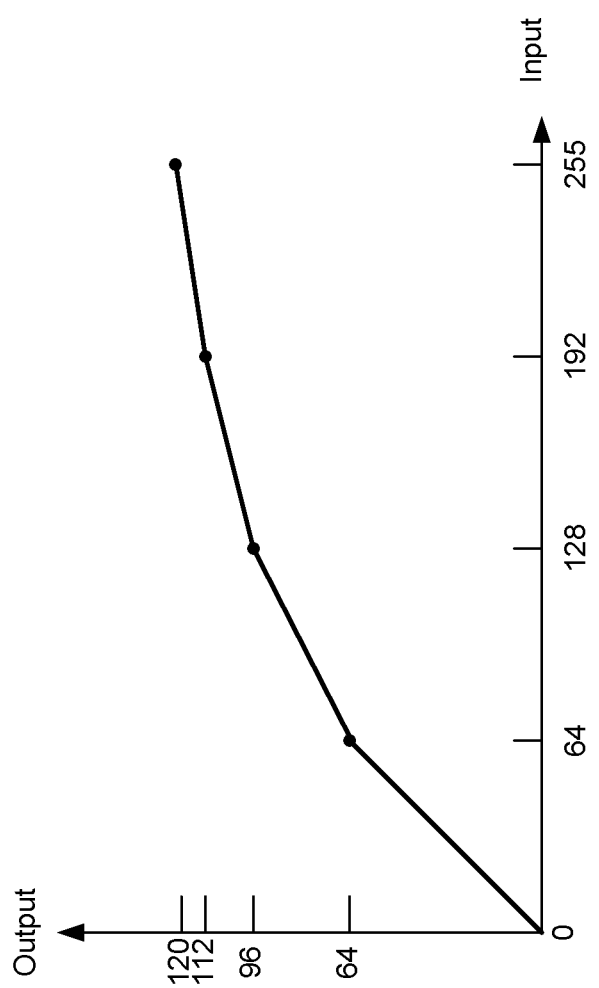
FIG. 3 illustrates an example of non-linear transformation using piece-wise linear curve.

In U.S. patent application Ser. No. 14/884,788, an embodiment to take a short structured light image in front of a regular image is disclosed as shown in FIG. 2. The timing signals related to the structured-light image are indicated in FIG. 2, where sli-reset corresponds to the structured-light image reset, sli-integration corresponds to the structured-light image integration and sli-readout corresponds to the structured-light image readout. The structured light duration is also indicated in FIG. 2, where the structured light is applied during the sli-integration. The whole period for capturing the structured-light image may occur during the reset period of a regular image reset. In the example shown in FIG. 2, the reset for the structured-light image may be very brief compared to the reset period for a regular image.

Since there is a small time difference between the structured-light image and the regular image, there may be small differences in the correspondence between the regular image and the depth information derived from the structured-light image. The discrepancy in the correspondences between the regular image and the depth information derived from the structured-light image can be detected and corrected by using another structured-light image taken in front of the above mention structured-light image or after the regular image. For example, the temporal sequence may correspond to SLI2→SLI1→RI or SLI1→RI→SLI2, where "SLI" represents "structured-light image" and "RI" represents "regular image". In one embodiment, the distance information for the regular image can be based on the depth information derived from SL1 and corrected by the difference between information derived from SL1 and information derived from SL2. The rationale for the derived depth information correction is based on the assumption that the magnitude of difference is linearly dependent on the time elapsed. The distance information for the regular image may also be based on the depth information derived from SL2 and corrected by the difference between depth information derived from SL2 and information derived from SL1.

In another embodiment, a depth information correction can be performed for each row. In the case of SLI1→RI→SLI2, for example, the time elapsed from row 1 of SLI1 to row 1 of RI may not be equal to the time elapsed from rowN (N>1) of SLI1 to rowN of RI. The derived depth information correction can be properly scaled for each lime instance to obtain improved depth information correction.

In yet another embodiment, the sequence may correspond to SLI1→SLI2→RI. According to SLI1 and SLI2, a depth model may be established and used to predict the depth information at the time instance corresponding to the regular image. In the case of SLI1→RI→SLI2, a depth model may be established between SLI1 and SLI2. The depth information for the regular image can be interpolated using the depth model derived based on SLI1 and SLI2. Again, the depth information prediction and interpolation can be operated on a row by row basis as mentioned above.

In the situation of a structured-light image captured in between two regular sub-images, i.e., captured sequence corresponding to sub-RI1→SLI→sub-RI2, an embodiment of the present invent may stretch the dynamic range of the combined regular image. Let $p_1(i, j)$ be the pixel value at location (i,j) of sub-RI1. If $p_1(i, j)$ has a value near the middle level (e.g. 128) for an 8-bit sensor, the pixel value at location (i,j) of sub-RI2, $p_2(i, j)$ should be substantially close to 128. If the integration times for the two regular sub-images are substantially the same and simple addition is used to combine the two sub-images, the pixel value of the combined regular image, p(i, j) will be 256, which results in a value at saturation and will be clamped to the maximum value of 255. If the pixel value at another location (i', j') is 138 for both sub-images, the corresponding combined pixel value would be 276 and clamped to 255. The two pixels will be both at maximum value while there is a noticeable difference between the two locations in the two regular sub-images.

In order to overcome the issue of signal saturation after combining the two sub-images, a non-linear pixel value transformation can be used before pixel value combination. In one embodiment, a predefined pixel value is selected. For example, the predefined value may correspond to the middle value of the full pixel range, such 128 for an 8-bit pixel data. A compression point may be selected as half of predefined pixel value. If the predefined value is 128, the compression point will be 64. In order to avoid saturation of combined pixel value, pixel values above the compression point will be "compressed" (i.e., reduced). For example, any pixel value for the sub-images over the compression point (i.e. 64 in the above example), the portion above the compression point will be compressed by dividing by 2. In this example, the corresponding pixel values of the two sub-images are processed by the non-linear transformation according to equation (1), where p'(i, j) is the transformed pixel value for the sub-images:

$$p'(i, j) = \begin{cases} p(i, j), & \text{if } p(i, j) \le 64, \\ 64 + (p(i, j) - 64)/2, & \text{if } p(i, j) > 64. \end{cases} \quad (1)$$

Therefore, when the corresponding pixel values for both sub-images are 128, the transformed pixel values become 64+(128−64)/2=96 and the combined value becomes 192. When the corresponding pixel values for both sub-images are 138, the transformed pixel values become 64+(138−64)/2=101 and the combined value becomes 202. After the non-linear transformation, the combined pixel values at two different locations can be differentiated as shown in the above example. Accordingly, the non-saturated combined pixel values can be extended to 191 for each sub-image if the corresponding pixels of the two sub-images have the same pixel value.

Other non-linear transformation may also be used. For example, a piece-wise linear curve may be used. For example, the transformation may correspond to no compression (i.e., no modification) for pixel range [0,64], compression by 2 for data range [65,128], compression by 4 for data range [129,192], and compression by 8 for data range [193, 255].

This method of detecting the difference between two regular sub-images and deciding whether to combine them or not can also be applied to any regular image capture without the intervening structured-light image. Therefore, a regular camera system can take advantage of dynamic range expansion by applying non-linear transformation to pixel values of sub-images and combining the sub-images. Furthermore, whether to combine the two regular sub-images into one combined regular image or to output one selected sub-image without combination can be determined based on the differences between the two sub-images or global motion vector/block motion vectors detected between the two sub-images.

Figure 4:
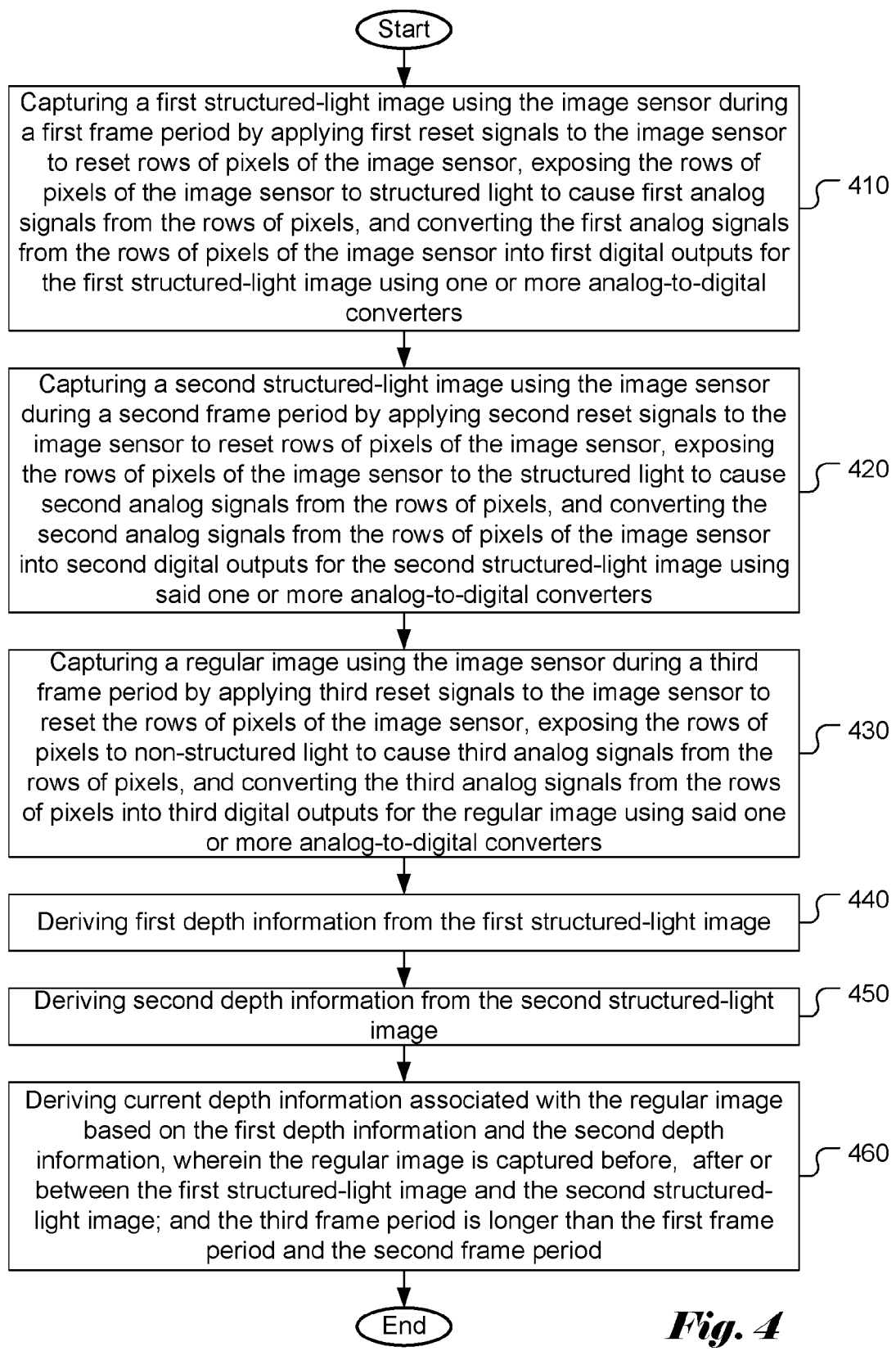
FIG. 4 illustrates an exemplary flowchart of depth information derivation for one regular image from structured-light images using a camera comprising an image sensor.

FIG. 4 illustrates an exemplary flowchart of depth information derivation for one regular image from structured-light images using a camera comprising an image sensor. According to this method, a first structured-light image is captured using the image sensor during a first frame period by applying first reset signals to the image sensor to reset rows of pixels of the image sensor, exposing the rows of pixels of the image sensor to structured light to cause first analog signals from the rows of pixels, and converting the first analog signals from the rows of pixels of the image sensor into first digital outputs for the first structured-light image using one or more analog-to-digital converters as shown in step 410. A second structured-light image is captured using the image sensor during a second frame period by applying second reset signals to the image sensor to reset rows of pixels of the image sensor, exposing the rows of pixels of the image sensor to the structured light to cause second analog signals from the rows of pixels, and converting the second analog signals from the rows of pixels of the image sensor into second digital outputs for the second structured-light image using said one or more analog-to-digital converters in step 420. A regular image is captured using the image sensor during a third frame period by applying third reset signals to the image sensor to reset the rows of pixels of the image sensor, exposing the rows of pixels to non-structured light to cause third analog signals from the rows of pixels, and converting the third analog signals from the rows of pixels into third digital outputs for the regular image using said one or more analog-to-digital converters in step 430. First depth information is derived from the first structured-light image in step 440. Second depth information is derived from the second structured-light image in step 450. Current depth information associated with the regular image is derived based on the first depth information and the second depth information in step 460, where the regular image is captured before, after or between the first structured-light image and the second structured-light image, and the third frame period is longer than the first frame period and the second frame period.

Figure 5:
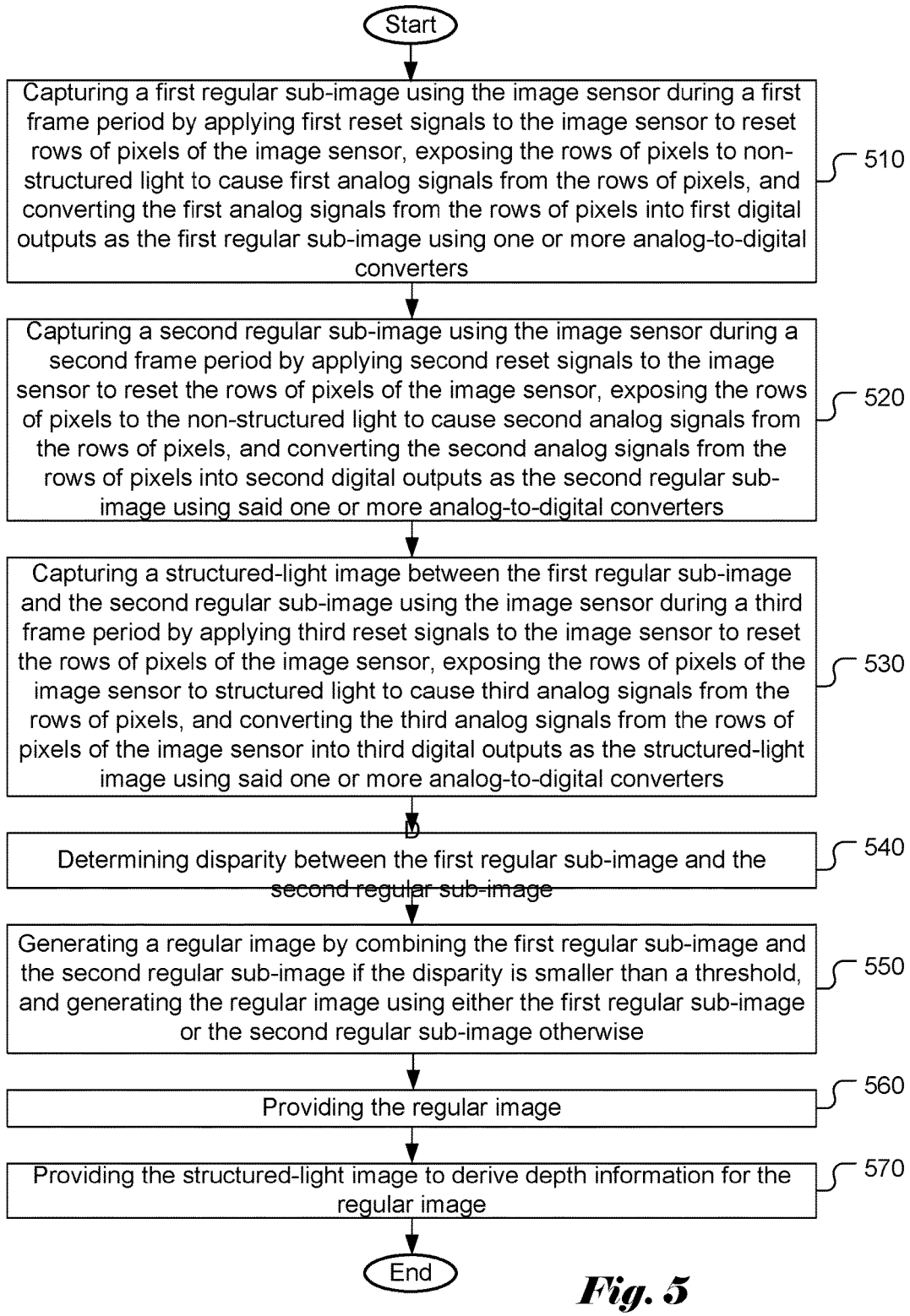
FIG. 5 illustrates another exemplary flowchart of depth information derivation for one regular image from structured-light images using a camera comprising an image sensor.

FIG. 5 illustrates an exemplary flowchart of depth information derivation for one regular image from structured-light images using a camera comprising an image sensor. According to this method, a first regular sub-image is captured using the image sensor during a first frame period by applying first reset signals to the image sensor to reset rows of pixels of the image sensor, exposing the rows of pixels to non-structured light to cause first analog signals from the rows of pixels, and converting the first analog signals from the rows of pixels into first digital outputs as the first regular sub-image using one or more analog-to-digital converters in step 510. A second regular sub-image is captured using the image sensor during a second frame period by applying second reset signals to the image sensor to reset the rows of pixels of the image sensor, exposing the rows of pixels to the non-structured light to cause second analog signals from the rows of pixels, and converting the second analog signals from the rows of pixels into second digital outputs as the second regular sub-image using said one or more analog-to-digital converters in step 520. A structured-light image between the first regular sub-image and the second regular sub-image is captured using the image sensor during a third frame period by applying third reset signals to the image sensor to reset the rows of pixels of the image sensor, exposing the rows of pixels of the image sensor to structured light to cause third analog signals from the rows of pixels, and converting the third analog signals from the rows of pixels of the image sensor into third digital outputs as the structured-light image using said one or more analog-to-digital converters in step 530. Disparity between the first regular sub-image and the second regular sub-image is determined in step 540. A regular image is generated by combining the first regular sub-image and the second regular sub-image if the disparity is smaller than a threshold, and generating the regular image using either the first regular sub-image or the second regular sub-image otherwise in step 550. The regular image is provided in step 560. The structured-light image is provided to derive depth information for the regular image in step 570.

Figure 6:
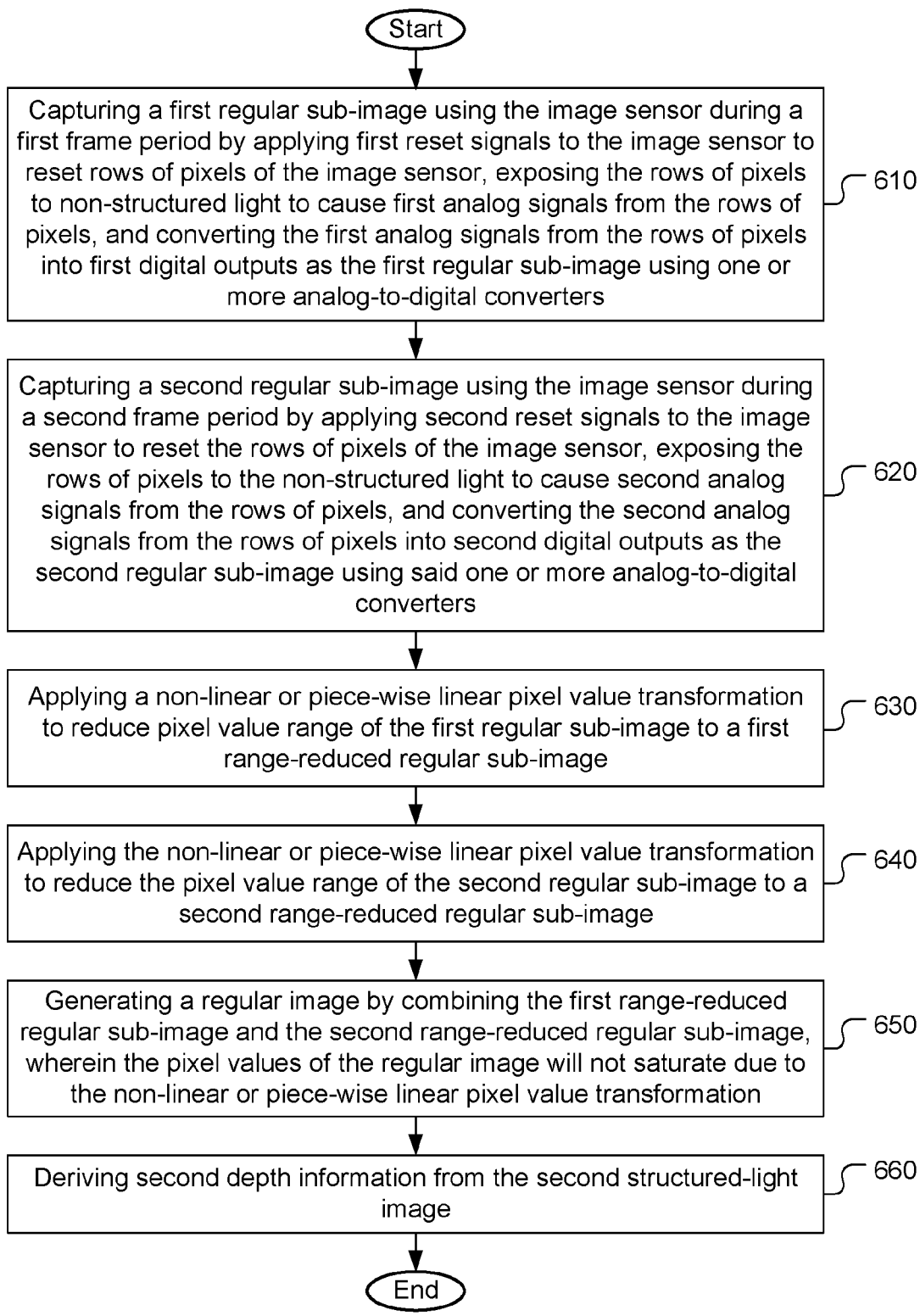
FIG. 6 illustrates an exemplary flowchart of generating one regular image from two regular sub-images using a camera comprising an image sensor.

FIG. 6 illustrates an exemplary flowchart of generating one regular image from two regular sub-images using a camera comprising an image sensor. According to this method, a first regular sub-image is captured using the image sensor during a first frame period by applying first reset signals to the image sensor to reset rows of pixels of the image sensor, exposing the rows of pixels to non-structured light to cause first analog signals from the rows of pixels, and converting the first analog signals from the rows of pixels into first digital outputs as the first regular sub-image using one or more analog-to-digital converters in step 610. A second regular sub-image is captured using the image sensor during a second frame period by applying second reset signals to the image sensor to reset the rows of pixels of the image sensor, exposing the rows of pixels to the non-structured light to cause second analog signals from the rows of pixels, and converting the second analog signals from the rows of pixels into second digital outputs as the second regular sub-image using said one or more analog-to-digital converters in step 620. A non-linear or piece-wise linear pixel value transformation is applied to reduce pixel value range of the first regular sub-image to a first range-reduced regular sub-image in step 630. A non-linear or piece-wise linear pixel value transformation is applied to reduce pixel value range of the second regular sub-image to a second range-reduced regular sub-image in step 640. A regular image is generated by combining the first range-reduced regular sub-image and the second range-reduced regular sub-image, wherein the pixel values of the regular image will not saturate due to the non-linear or piece-wise linear pixel value transformation in step 650. The regular image is provided in step 660.

The invention may be embodied in other specific forms without departing from its spirit or essential characteristics. The described examples are to be considered in all respects only as illustrative and not restrictive. Therefore, the scope of the invention is indicated by the appended claims rather than by the foregoing description. All changes which come within the meaning and range of equivalency of the claims are to be embraced within their scope.

The invention claimed is:

1. A method of deriving depth information for a regular image from structured-light images using a camera comprising an image sensor, the method comprising:

projecting a first structured light to a scene in a field of view of the image sensor, wherein the image sensor comprises a pixel array;

applying first reset signals to the pixel array to reset rows of the pixel array;

exposing the rows of the pixel array to the first structured light to cause first analog signals from the rows of the pixel array;

capturing a first structured-light image using the pixel array during a first frame period by converting the first analog signals from the rows of the pixel array into first digital outputs to form the first structured-light image using one or more analog-to-digital converters;

projecting a second structured light to the scene in the field of view of the image sensor;

applying second reset signals to the pixel array to reset rows of the pixel array;

exposing the rows of the pixel array to the second structured light to cause second analog signals from the rows of the pixel array;

capturing a second structured-light image using the pixel array during a second frame period by converting the second analog signals from the rows of the pixel array into second digital outputs to form the second structured-light image using said one or more analog-to-digital converters;

applying third reset signals to the pixel array to reset the rows of the pixel array;

exposing the rows of the pixel array to non-structured light to cause third analog signals from the rows of the pixel array;

capturing the regular image using the pixel array during a third frame period by converting the third analog signals from the rows of the pixel array into third digital outputs to form the regular image using said one or more analog-to-digital converters;

deriving first depth information from the first structured-light image;

deriving second depth information from the second structured-light image; and deriving current depth information associated with the regular image based on the first depth information and the second depth information; and wherein same pixels of the pixel array are used for capturing the first structured-light image, the second structured-light image and the regular image;

wherein the regular image is captured before, after or between the first structured-light image and the second structured-light image; and wherein the third frame period is longer than the first frame period and the second frame period.

2. The method of claim 1, wherein when the regular image is captured between the first structured-light image and the second structured-light image, the current depth information is derived based on the first depth information and differences between the first depth information and the second depth information, or based on the second depth information and the differences between the first depth information and the second depth information.

3. The method of claim 1, wherein the current depth information is derived row by row based on the first depth information and differences between the first depth information and the second depth information by taking into account of time elapsed between each corresponding rows in the first structured-light image and the regular image respectively, or based on the second depth information and the differences between the first depth information and the second depth information by taking into account of time elapsed between each corresponding rows in the second structured-light image and the regular image respectively.

4. The method of claim 1, wherein a depth model is derived based on the first depth information and the second depth information, and the current depth information is derived using the depth model.

5. The method of claim 4, wherein when the regular image is captured between the first structured-light image and the second structured-light image, the current depth information is interpolated using the depth model.

6. The method of claim 4, wherein when the regular image is captured after the first structured-light image and the second structured-light image, the current depth information is predicted using the depth model.

7. A capsule camera system, comprising:

an image sensor comprising a pixel array being responsive to light energy received by the image sensor to produce pixel signals having a voltage level depending on the light energy received;

a structured light source;

a non-structured light source;

one or more output circuits coupled to the image sensor to access the pixel signals produced by the image sensor;

one or more analog-to-digital converters having a first dynamic range and a second dynamic range;

one or more timing and control circuits, wherein said one or more timing and control circuits are arranged to:

project a first structured-light to a scene in a field of view of the image sensor;

apply first reset signals to the pixel array to reset rows of the pixel array;

expose the rows of the pixel array to the first structured light to cause first analog signals from the rows of the pixel array;

capture a first structured-light image using the image sensor during a first frame period by converting the first analog signals from the rows of the pixel array into first digital outputs to form the first structured-light image using one or more analog-to-digital converters;

project a second structured light to the scene in the field of view of the image sensor;

apply second reset signals to the pixel array to reset rows of the pixel array;

expose the rows of the pixel array to the second structured light to cause second analog signals from the rows of the pixel array;

capture a second structured-light image using the image sensor during a second frame period by converting the second analog signals from the rows of the pixel array into second digital outputs to form the second structured-light image using said one or more analog-to-digital converters;

apply third reset signals to the pixel array to reset the rows of the pixel array;

exposing the rows of the pixel array to non-structured light to cause third analog signals from the rows of the pixel array, and capture a regular image using the image sensor during a third frame period by converting the third analog signals from the rows of the pixel array into third digital outputs to form the regular image using said one or more analog-to-digital converters;

derive first depth information from the first structured-light image;

derive second depth information from the second structured-light image; and derive current depth information associated with the regular image based on the first depth information and the second depth information; and wherein same pixels of the pixel array are used for the first structured-light image, the second structured-light image and the regular image;

wherein the regular image is captured before, after or between the first structured-light image and the second structured-light image; and wherein the third frame period is longer than the first frame period and the second frame period.

* * * * *